United States Patent [19]

Mich et al.

[11] Patent Number: 4,617,308
[45] Date of Patent: Oct. 14, 1986

[54] 7-SUBSTITUTED AMINO-1-ARYL-6,8-DIFLUORO-1,4-DIHYDRO-4-OXO-3-QUINOLINECARBOXYLIC ACIDS AND DERIVATIVES THEREOF AS ANTIBACTERIAL AGENTS

[75] Inventors: Thomas F. Mich, Ann Arbor; John M. Domagala, Canton, both of Mich.

[73] Assignee: Warner-Lambert Company, Morris Plains, N.J.

[21] Appl. No.: 695,145

[22] Filed: Jan. 25, 1985

[51] Int. Cl.[4] ..................... A61K 31/97; C07D 215/27
[52] U.S. Cl. .................................. 514/312; 514/278; 546/15; 546/16; 546/156
[58] Field of Search .................. 546/15, 16, 156; 514/312, 278

[56] References Cited

U.S. PATENT DOCUMENTS

| 4,398,029 | 8/1983 | Irikura | 546/156 |
| 4,530,930 | 7/1985 | Uno | 546/156 |
| 4,550,103 | 10/1985 | Mich | 546/16 |
| 4,550,104 | 10/1985 | Mich | 546/16 |

FOREIGN PATENT DOCUMENTS

| 0131839 | 1/1985 | European Pat. Off. | 546/156 |
| 0086476 | 7/1976 | Japan | 514/312 |
| 0040656 | 3/1980 | Japan | 514/312 |
| 1147336 | 4/1969 | United Kingdom | 546/156 |

Primary Examiner—Esther M. Kepplinger
Assistant Examiner—Robert Benson
Attorney, Agent, or Firm—Ronald A. Daignault

[57] ABSTRACT

Novel 1-aryl or heteroaryl-6,8-difluoro-1,4-dihydro-7-(3-aminomethyl)pyrrolidinyl- or 7-spiroamino-4-oxo-3-quinolinecarboxylic acids and acid derivatives thereof as antibacterial agents are described as well as methods for their manufacture, formulation and use in treating bacterial infections caused by Gram-negative and Gram-positive bacteria.

12 Claims, No Drawings

7-SUBSTITUTED AMINO-1-ARYL-6,8-DIFLUORO-1,4-DIHYDRO-4-OXO-3-QUINOLINECARBOXYLIC ACIDS AND DERIVATIVES THEREOF AS ANTIBACTERIAL AGENTS

BACKGROUND OF THE INVENTION

European Patent Publication 106,489 discloses certain 7-substituted 1,4-dihydro-4-oxo-quinolines and naphthyridines having similar substituents on the 7-position as the compounds of the instant invention as antibacterial agents.

1-Phenyl-1-quinoline-3-carboxylic acids are described in U.K. Patent Specification No. 1,147,336 as having antiinflammatory and antibacterial activity.

Naphthyridine-3-carboxylic acids having anti-bacterial, sedative, and stimulator activities are described in U.S. Pat. No. 3,590,036.

Abstracts of the 1984 ICAAC meeting disclose derivatives of 1-phenyl-6-fluoro-7-substituted 1,4-dihydro-4-oxo-1,8-naphthyridine-3-carboxylic acid where the substituted amino group is piperazine, and 1-aryl-6-fluoroquinolones such as a compound of the formula

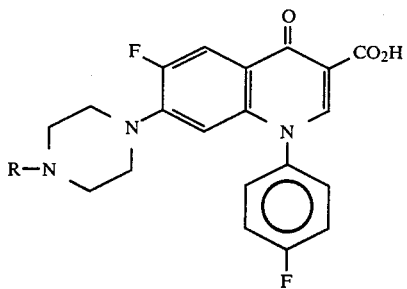

where R is H or $CH_3$. These are also said to have antibacterial activity.

SUMMARY OF THE INVENTION

The present invention in a first generic chemical compound aspect is a compound having the structural formula I

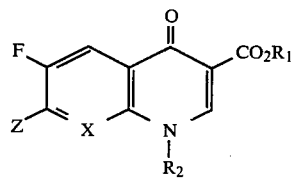

wherein Z is

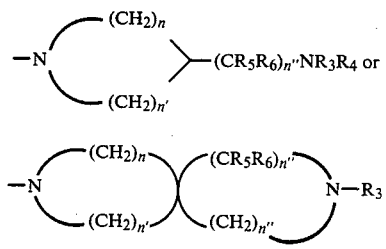

X is CH, CF, or N; n is 1, 2, 3, or 4; n' is 1, 2, 3, or 4 wherein n+n' is a total of 2, 3, 4, or 5, and n" is 0, 1, or 2; $R_1$ is hydrogen, alkyl having from one to six carbon atoms or a cation; $R_2$ is aryl or heteroaryl; $R_3$ is hydrogen, alkyl having from one to four carbon atoms or cycloalkyl having three to six carbon atoms; $R_4$ is hydrogen, alkyl from one to four carbon atoms, hydroxyalkyl having two to four carbon atoms, trifluoroethyl or $R_7CO$— wherein $R_7$ is alkyl having from one to four carbon atoms, or alkoxy having from one to four carbon atoms; $R_5$ is hydrogen, or alkyl having from one to three carbon atoms; $R_6$ is hydrogen or alkyl having from one to three carbon atoms; and the pharmaceutically acceptable acid addition or base salts thereof.

The invention also includes a pharmaceutical composition which comprises an antibacterially effective amount of a compound having structural formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The term, aryl, is intended to include a phenyl group substituted by halogen, alkyl, alkoxy, hydroxy, amino, monoalkylamino, dialkyamino or trifluoromethyl. Preferred substituents are in the para-position and are fluoro, amino, monoalkyl or dialkylamino. Most preferred is the para-fluoro substituent.

The term, heteroaryl, is intended to mean an aromatic ring having one or more hetero-atoms such as nitrogen, oxygen, and sulfur. Representative are 2-, 3-, or 4-pyridine, 2- or 3-thiophene, 2-imidazole, 2-oxazole, and 2-thiazole.

The alkyl groups contemplated by the invention comprise both straight and branched carbon chains of from one to about six carbon atoms unless otherwise stated. Representative of such groups are methyl, ethyl, propyl, isopropyl, and the like.

The cycloalkyl groups contemplated by the invention comprise those having three to six carbons atoms such as cyclopropyl, cyclobutyl, cyclopentyl, and cyclohexyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The terms monoalkylamino and dialkylamino are intended to include amino substituted by one or two alkyl groups as defined above where each group is the same or different. Representative of such groups are methylamino, ethylamino, dimethylamino, diethylamino, methylethylamino, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional asymmetric carbon atoms may be present in a substituent such as an alkyl group. All such isomers as well as mixtures thereof are intended to be included in the invention.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, silver, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The preferred compounds of this invention are those wherein Z is

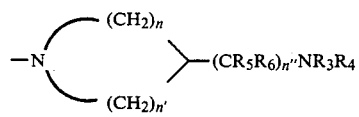

Also preferred compounds of this invention are those wherein Z is

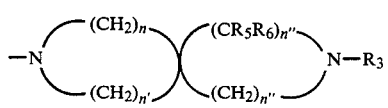

Other preferred compounds of this invention are those wherein $R_1$ is hydrogen or a pharmaceutically acceptable base salt such as a metal or amine salt.

Other preferred compounds of this invention are those wherein $R_2$ is phenyl, p-fluorophenyl, 2-thiazole, or 2-, 3-, or 4-pyridine.

The most preferred compounds are those wherein X is N or CF, Z is

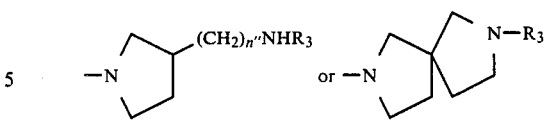

$R_1$ is hydrogen, $R_2$ is phenyl, p-fluorophenyl, or 2-thiazole; n' is 0 or 1 and $R_3$ is hydrogen, methyl, ethyl, 1- or 2-propyl, or a pharmaceutically acceptable acid addition or base salt thereof.

Particularly preferred species of the invention are the compounds having the names:

7-[3[(ethylamino)methyl]-1-pyrrolidinyl]-6,8-difluoro-1,4-dihydro-4-oxo-1-phenyl-3-quinoline-carboxylic acid;

7-[3-(aminomethyl)-1-pyrrolidinyl]-6,8-difluoro4-oxo-1-phenyl-3-quinolinecarboxylic acid;

7-[3-[(ethylamino)methyl]-1-pyrrolidinyl]-6,8-difluoro-1-(4-fluorophenyl)-1,4-dihydro-4-oxo-3-quinolinecarboxylic acid;

7-[3-amino-1-pyrrolidinyl]-6,8-difluoro-1-(4-fluorophenyl)-1,4-dihydro-4-oxo-3-quinolinecarboxylic acid; and 7-[3-(aminomethyl)-1-pyrrolidinyl]-6,8-difluoro1-(4-fluorophenyl)-1,4-dihydro-4-oxo-3-quinolinecarboxylic acid.

The following is a process for preparing a compound of the formula

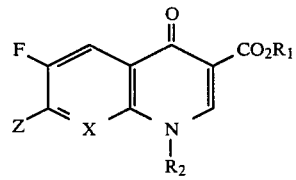

wherein $R_1$, $R_2$, X, and Z are as defined above which comprises reacting a compound having the following formula

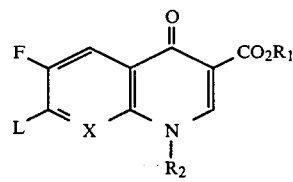

II with an amine corresponding to the group Z wherein Z is the compound having the structural formula

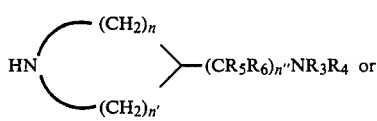

IIIa

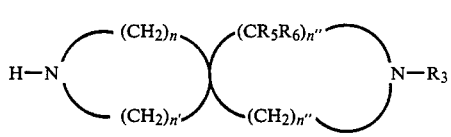

IIIb wherein all of the above terms are as defined in formulae I and L is a leaving group which is preferably fluorine or chlorine.

The compounds of the invention having the structural formula I may be readily prepared by treating a corresponding compound having the structural formula II with the desired cyclic amine IIIa or IIIb. For purposes of this reaction, the alkylamine substituent of Compound IIIa or IIIb may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, β,β,β-trichloroethoxycarbonyl, β-iodoethoxycarbonyl; aryloxycarbonyl groups such as benzyloxycarbonyl, p-methoxybenzyloxycarbonyl, phenoxycarbonyl; silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound II and Compound IIIa or IIIb if desired, by procedures known to those skilled in the art. For example, the ethoxycarbonyl group may be removed by acid or base hydrolysis and the benzyl group may be removed by hydrogenolysis.

The reaction between the compound of structural formula II and a suitably protected compound of formula IIIa or IIIb, may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of formula III may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group $R_4$ may be accomplished either before or after isolating the product, I. Alternatively, the protecting group $R_4$ need not be removed.

The starting compounds having structural formula II, wherein X is CH and L is Cl, may be prepared as described in European Patent Publication No. 78,362. For example, a representative compound of the formula

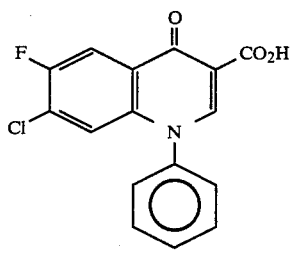

IV is prepared by reacting aniline with a compound of the formula

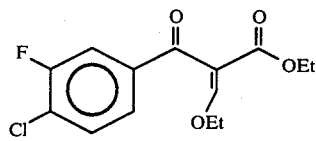

The naphthyridines of formula II, i.e., when X is N and L is Cl are prepared in the same manner as above described and referred to in European Patent Publication No. 78,362 by converting by known means 2,6-dichloro-3-cyano-5-fluoropyridine to a corresponding compound to formula V which precursor is reacted with the appropriate aryl or heteroaryl amine.

The starting compound of formula II, wherein X is CF and L is F, namely aryl- or heteroaryl-6,7,8-trifluoro-1,4-dihydro-4-oxo-3-quinolinecarboxylic acid may be prepared by a series of reactions starting from 2,3,4,5-tetrafluorobenzoic acid and detailed also in the Preparative Examples. The acid chloride of 2,3,4,5-tetrafluorobenzoic acid is reacted with dilithio malonic acid mono ethyl ester to afford after hydrolysis 2,3,4,5-tetrafluoro-β-oxo-benzenepropanoic acid ethyl ester. This compound is, successively, treated with triethylorthoformate and acetic anhydride, the appropriate aryl or heteroarylamine, potassium-t-butoxide, and aqueous hydrochloric acid to give the desired intermediate.

The compounds of the invention having structural formula IIIa or IIIb are either known compounds or they may be prepared from known starting materials by standard procedures or by variations thereof. For example, 3-pyrrolidinemethanamines having the structural formula D

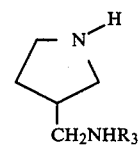

may be readily prepared from the known starting material methyl 5-oxo-1-(phenylmethyl)-3-pyrrolidinecarboxylate, A, [J. Org. Chem., 26, 1519 (1961)] by the following reaction sequence.

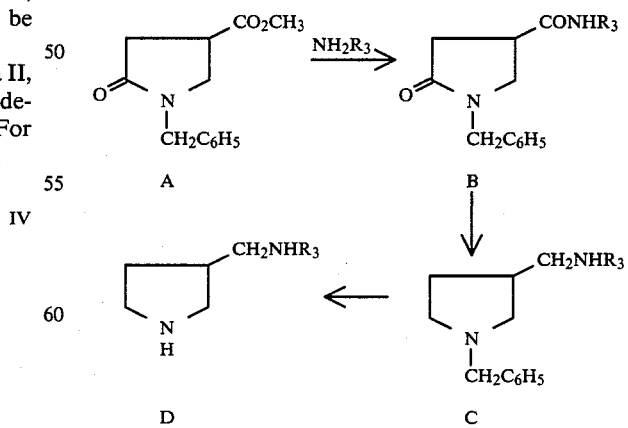

The compound wherein $R_3$ is hydrogen, namely 3-pyrrolidinemethanamine, has been reported in J. Org. Chem., 26, 4955 (1961).

Thus Compound A may be converted to the corresponding amide B by treatment with $R_3NH_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R=H in C, the primary amine function may be protected with a group $R_4$ as defined, hereinabove. For example, the primary amine function may be acylated with an acyl halide such as acetyl chloride by well known procedures. The primary amine function of C may also be converted to a carbamate ester such as the ethyl ester by treatment with ethyl chloroformate in the presence of a strong base such as 1,8-diazabicyclo[5.4.0]undec-7-ene in a convenient solvent such as methylene chloride. The benzyl group may next be removed, for example as described above for Compound C, thereby producing Compound D where R is $-CO_2Et$, which after conversion to a compound of the type IIIa or IIIb may be reacted with a compound having the structural formula II to thereby produce a corresponding compound having the structural formula I. The $-CO_2Et$ group may be removed by standard procedures.

Likewise spiroamino compounds represented by structural formula IIIb may be readily prepared from the known starting material 3-ethoxycarbonyl-5-oxo-3-pyrrolidineacetic acid ethyl ester [J. Org. Chem., 46, 2757 (1981)] by the following reaction sequence.

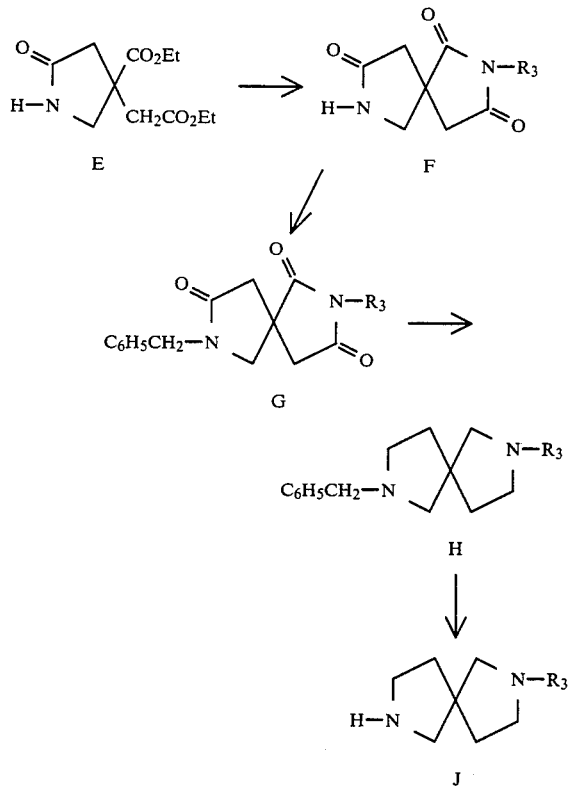

The compound 2,7-diazaspiro [4.4]nonane where $R_3$ is H is described in the above reference. Thus compound E may be converted to the corresponding amide F by treatment with $R_3NH_2$, for example, methyl amine in water followed by benzylation which may be carried out with sodium hydride and benzyl chloride to give G. Reduction to the diamine H may be accomplished with lithium aluminum hydride. Subsequent debenzylation, for example, with hydrogen and 20% palladium on carbon catalyst produces the diamine J.

The compounds of the invention display anti-bacterial activity when tested by the microtitration dilution method as described in Heifetz, et al, Antimicr. Agents & Chemoth., 6, 124 (1974), which is incorporated herein by reference and illustrated in the following table.

| Organisms | IN VITRO ANTIBACTERIAL ACTIVITY Minimal Inhibitory Concentration MIC (μ/ml) | | |
|---|---|---|---|
| | Compound Ex. 1 | Compound Ex. 3 | Compound Ex. 4 |
| *Enterobacter cloacae* MA 2646 | 0.8 | 1.6 | 0.4 |
| *Escherichia coli* Vogel | 0.8 | 1.6 | 0.2 |
| *Klebsiella pneumoniae* MGH-2 | 1.6 | 1.6 | 0.8 |
| *Proteus rettgeri* M 1771 | 1.6 | 6.3 | 1.6 |
| *Pseudomonas aeruginosa* UI-18 | 1.6 | 6.3 | 1.6 |
| *Staphylococcus aureus* H 228 | 0.1 | 0.8 | 0.2 |
| *Staphylococcus aureus* UC-76 | 0.2 | 0.2 | 0.1 |
| *Streptococcus faecalis* MGH-2 | 0.2 | 0.8 | 0.2 |
| *Streptococcus pneumoniae* SV-1 | 0.4 | 1.6 | 0.2 |
| *Streptococcus pyogenes* C-203 | 0.4 | 1.6 | 0.2 |

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

PREPARATION OF STARTING MATERIALS

EXAMPLE A 2,3,4,5-Tetrafluoro-β-oxo-benzenepropanoic acid, ethyl ester

To 30.0 g (155 mmol) of 2,3,4,5-tetrafluorobenzoic acid in 75 ml of dichloromethane was added 14.8 ml (1.1 equivalents) of oxalyl chloride. The mixture was then treated with three drops of dry N,N-dimethylformamide and the vigorous reaction was stirred at room temperature overnight. The mixture was then concentrated to an oil, was taken up in toluene, and reconcentrated to afford 2,3,4,5-tetrafluorobenzoyl chloride which was used in the next step.

To 40.92 g (310 mmol) of malonic acid half ethyl ester in 700 ml of dry tetrahydrofuran at −35° was added a stream of n-butyllithium until one equivalent was delivered. The mixture was maintained at −15° to −30° during addition, and was warmed to −5° when 10 mg of bipyridyl was added. The remainder of the n-butyllithium was added at this temperature until the indicator turned pink. A total of 282 ml of 2.2 N n-butyllithium was added. The mixture was recooled to -78° C. and a solution of 2,3,4,5-tetrafluorobenzoyl chloride was added in 100 ml of dry tetrahydrofuran keeping the temperature constant. The reaction mixture was stirred 45 minutes after the complete acid chloride addition. It was warmed to −35° C. and poured into 155 ml of 2N hydrochloric acid. To this mixture was added one liter of water and 1.5 liters of dichloromethane. The aqueous phase was separated and extracted with an additional 1.5 liters of dichloromethane. The combined organic phases were washed with 50% saturated sodium bicarbonate and then 1N hydrochloric acid. The dichloromethane was dried (magnesium sulfate) and concentrated to a solid which was triturated with cold pentane to give 37.8 g of 2,3,4,5-tetrafluoro-β-oxobenzenepropanoic acid, ethyl ester, mp 63°-65° C.

EXAMPLE B 6,7,8-Trifluoro-1-(4-fluorophenyl)-1,4-dihydro-4-oxo-3-quinoline carboxylic acid To 3.0 g (11.33 mmol) of (2,3,4,5-tetrafluoro-β-oxobenzenepropanoic acid, ethyl ester was added 2.49 g of triethylorthoformate and 2.76 g of acetic anhydride. The mixture was refluxed for 2.5 hours and was concentrated under high vacuum at 80° C. to dryness. The residual oil was treated, at 45° C., with 1.32 g (1.05 equivalents) of 4-fluoroaniline dissolved in 25 ml of t-butanol. After two hours the mixture was treated with 1.33 g (1.0 equivalent) of potassium tert-butoxide dissolved in 15 ml of t-butanol added dropwise over a fifteen minute period. After 24 hours the reaction mixture was cooled to room temperature and treated with 0.25 ml acetic acid and 100 ml of isopropanol. The mixture was stirred ten minutes and then concentrated. The resulting solids were titrated with isopropanol. Filtration afforded 2.24 g of the crude product, ethyl 6,7,8-trifluoro-1-(4-fluorophenyl)-1,4-dihydro-4-oxo-3-quinolinecarboxylate.

Without further purification, 2.2 g (6.03 mmol) of the ethyl 6,7,8-trifluoro-1-(4-fluorophenyl)-1,4-dihydro-4-oxo-3-quinolinecarboxylate was treated with 20 ml of hot acetic acid and 10 ml of 2N hydrochloric acid, then heated at 100° C. for two hours. The mixture was then filtered and the resulting solid washed with water to give 1.22 g of 6,7,8-trifuloro-1-(4-fluorophenyl)-1,4-dihydro-4-oxo-3-quinoline carboxylic acid, mp 255°-257° C.

EXAMPLE C 6,7,8-Trifluoro-1,4-dihydro-4-oxo-1-phenyl-3-quinoline carboxylic acid To 3.0 g (11.33 mmol) of 2-(2,3,4,5-tetrafluorobenzoyl)acetic acid, ethyl ester was added 2.49 g of triethylorthoformate and 2.76 g of acetic anhydride. The mixture was refluxed for two hours and was concentrated under high vacuum at 80° C. to dryness. The residual oil was treated with 1.05 g (1.0 equivalent) of aniline dissolved in 70 ml of isopropyl alcohol. After 24 hours the mixture was concentrated and the solid triturated with hexane. Filtration gave 2.88 g of 2,3,4,5,-tetrafluoro-β-oxo-α-1-ethoxyethylidene-phenylpropanoic acid, ethyl ester, mp 101°-103° C.

Without further purification this material was placed in 100 ml of dry dioxane 0.395 g of 50% sodium hydride oil dispersion. The mixture was stirred for 20 minutes at room temperature and 2.5 hour at 100° C. The reaction mixture was concentrated to dryness and the solid taken up in dichloromethane and washed with dilute hydrochloric acid. The dichloromethane was then dried (magnesium sulfate) and was concentrated. The solids were washed with ether:pentane (1:1) to give 2.56 g of crude product. This material was purified by column chromatography (silica gel, chloroform:hexane:isopropanol - 5.5:3.5:1) to give 2.13 g of 6,7,8-trifluoro-1,4-dihydro-4-oxo 1-phenyl-3-quinolinecarboxylic acid, ethyl ester, mp 190.5°-192°. This product was dissolved in 60 ml of hot acetic acid and 30 ml of 2N hydrochloric acid was added. The reaction was heated to 100° C. for 1.5 hours and was allowed to cool slowly to room temperature. Filtration gave 1.88 g of 6,7,8-trifluoro-1,4-dihydro-4-oxo-1-phenyl-3-quinolinecarboxylic acid, mp 264°-267.5° C.

EXAMPLE D 6,7,8-Trifluoro-1,4-dihydro-4-oxo-1-(2-thiazolyl)3-quinolinecarboxylic acid To 3.0 g (11.33 mmol) of 2,3,4,5-tetrafluoro-β-oxobenzeneproprionic acid, ethyl ester was added 2.49 g of triethylorthoformate and 2.76 g of acetic anhydride. The mixture was refluxed for two hours and concentrated to dryness under high vacuum at 80° C. The residual oil was treated with 1.32 g (1.2 equivalents) of 2-aminothiazole suspended in 70 ml of isopropanol. At 70° C., 1.6 g (1.0 equivalent) of 1,8-diazobicyclo[5.4.0]undec-7-ene was added. After 18 hours, the mixture was cooled and filtered to give 2.73 g of the 6,8,7-trifluoro-1,4-dihydro-4-oxo-1-(2-thiazolyl)-3-quinolinecarboxylic acid, ethyl ester, mp 172°-174° C. This material was dissolved in 100 ml of hot acetic acid and 50 ml of 2N hydrochloric acid and was heated at 100° C. for 2.5 hours. The mixture was cooled, partially concentrated, and filtered to give 1.81 g of 6,7,8-trifluoro-1,4-dihydro-4-oxo-1-(2-thiazolyl)-3-quinolinecarboxylic acid, mp 198.5°-200° C.

EXAMPLE E 1,1-Dimethylethyl (3-Pyrrolidinyl)carbamate 1,1-Dimethylethyl [1-(Phenylmethyl)-3-pyrrolidinyl]-carbamate A solution of 77.0 g (0.44 mole) of 3-amino-1-(phenylmethyl)pyrrolidine [*J. Med. Chem.*, 24, 1229 (1981)], 440 ml (0.44 mole) 1N sodium hydroxide and 600 ml of tertiary butyl alcohol was treated dropwise with 98.2 g (0.45 mole) of di-tertiarybutyl dicarbamate. The reaction was stirred at room temperature for 18 hours and the solvent removed in vacuo. The residue was partitioned between ether and water. The aqueous layer was reextracted with ether, the combined ether layers were washed with water, dried (MgSO₄), filtered and evaporated on a steam bath replacing the ether with petroleum ether. The crystals which formed were removed by filtration, washed with ether/petroleum ether (1:1), and dried in vacuo to give 84.8 g of 1,1-dimethylethyl [1-(phenylmethyl)-3-pyrrolidinyl]carbamate, mp 114°-115°. A second crop (16.7 g) was obtained by concentrating the filtrate.

1,1-Dimethylethyl (3-Pyrrolidinyl)carbamate

A mixture of 27.6 g (0.1 mole) of 1,1-dimethylethyl[1-(phenylmethyl)-3-pyrrolidinyl]carbamate, 1.0 g of 20% Palladium on carbon and 140 ml of methanol was shaken in an atmosphere of hydrogen at about 50 psi and room temperature for 24 hours. The catalyst was removed by filtering through Celite, and the filtrate was concentrated in vacuo to give 18.4 g of 1,1-dimethylethyl (3-pyrrolidinyl)carbamate which solidified upon standing.

EXAMPLE 1

7-[3-[Ethylamino)methyl]-1-pyrrolidinyl]6,8-difluoro-1-(4-fluorophenyl)-1,4-dihydro-4-oxo-3-quinolinecarboxylic acid To 0.62 g (1.8 mmol) of 6,7,8-trifluoro-1-(4-fluorophenyl)-1,4-dihydro-4-oxo-3-quinolinecarboxylic acid in 15 ml of acetonitrile was added 0.23 g (1.0 equivalent) of N-ethyl-3-pyrrolidinemethanamine and 0.28 g (1.0 equivalent) of 1,8-diazobicyclo [5.4.0]undec-7-ene in 5 ml of acetonitrile. The reaction was refluxed for one hour and then checked by thin layer chromatography. Excess (10%) N-ethyl-3-pyrrolidine methanamine was added as necessary and the mixture heated to reflux for an additional two hours. The solids were then filtered and washed with ether to give 0.70 g of 7-[3-[(ethylamino)methyl]-1-pyrrolidinyl]-6,8-difluoro-1-(4-fluorophenyl)-1,4-dihydro-4-oxo-3-quinoline carboxylic acid, mp 249°-251° C.

Using the above procedure with 3-pyrrolidine methanamine, 7-[3-(aminomethyl)-1-pyrrolidinyl]-6,8-difluoro-1-(4-fluorophenyl)-1,4-dihydro-4-oxo-3-quinolinecarboxylic acid may also be prepared.

EXAMPLE 2

7-[3[(Ethylamino)methyl]-1-pyrrolidinyl]-6,8-difluoro-1,4-dihydro-4-oxo-1-(2-thiazolyl)-3-quinolinecarboxylic acid To 1.0 g (3.06 mmol) of the 6,7,8-trifluoro-1,4-dihydro-4-oxo-1-(2-thiazolyl)-3-quinolinecarboxylic acid in 10 ml of acetonitrile was added 0.46 g of 1,8-diazobicyclo[5.4.0]undec-7-ene and 0.39 g of 3-[(ethylamino)methyl]pyrrolidine. The reaction was warmed to 60° C. for one hour and was then taken to room temperature and stirred overnight. The solids were filtered and washed with ether to give 0.32 g of 7-[3[(ethylamino)methyl]-1-pyrrolidinyl]-6,8-difluoro-1,4-dihydro-4-oxo-1-(2-thiazolyl)-3-quinolinecarboxylic acid, mp 200°-207° (dec).

EXAMPLE 3

7-[3-[(Ethylamino)methyl]-1-pyrrolidinyl]-6,8-difluoro-1,4-dihydro-4-oxo-1-phenyl-3-quinolinecarboxylic acid To 0.88 g (2.75 mmol) of the 6,7,8-trifluoro-1,4-dihydro-4-oxo-1-phenyl-3-quinolinecarboxylic acid in 15 ml of acetonitrile was added 0.418 g (1.05 equivalents) of 1,8-diazobicyclo[5.4.0]undec-7-ene and 0.32 g (1.0 equivalent) of 3-[(ethylamino)methyl]-pyrrolidine. The reaction was refluxed for one hour and was stirred overnight at room temperature. The mixture was filtered to give 0.75 g of 7-[3-(ethylamino)methyl]-1-pyrrolidinyl]-6,8-difluoro-1,4-dihydro-4-oxo-1-phenyl-3-quinolinecarboxylic acid, mp 258°-260° C.

EXAMPLE 4

7-[3-(Aminomethyl)-1-pyrrolidinyl]-6,8-difluoro-1,4-dihydro-4-oxo-1-phenyl-3-quinoline carboxylic acid Using the identical procedure described above 0.88 g of 6,7,8-trifluoro-1,4-dihydro-4-oxo-1-phenyl-3-quinolinecarboxylic acid was converted to 0.76 g of 7-[3-(aminomethyl)-1-pyrrolidinyl]6,8-difluoro-1,4-dihydro-4-oxo-1-phenyl-3-quinolinecarboxylic acid, mp 247–251.

EXAMPLE 5

7-[3-Amino-1-pyrrolidinyl]-6,8-difluoro-1-(4-fluorophenyl)-1,4-dihydro-4-oxo-3-quinolinecarboxylic acid

7-[3-t-Butoxycarbonylamino-1-pyrrolidinyl]-6,8-difluoro-1-(4-fluorophenyl)-1,4-dihydro-4-oxo-3-quinolinecarboxylic acid A mixture of 1.24 g (3.6 mmol) of 6,7,8-trifluoro-1-(4-fluorophenyl)-1,4-dihydro-4-oxo-3-quinolinecarboxylic acid, 1.0 g (5.4 mmol) of 1,1-dimethylethyl (3-pyrrolidinyl)carbamate, 0.56 g (3.6 mmol) of 1,8-dizabicyclo[5.4.0]undec7-ene, and 25 ml of acetonitrile is heated at reflux for four hours and is allowed to stir at room temperature overnight. The precipitated solids are filtered washed with ether to give 7-[3-t-butoxycarbonylamino-1-pyrrolidinyl]-6,8-difluoro-1-(4-fluorophenyl)-1,4-dihydro-4-oxo-3-quinoline carboxylic acid.

7-[3-Amino-1-pyrrolidinyl]-6,8-difluoro-1-(4-fluorophenyl)-1,4-dihydro-4-oxo-3-quinolinecarboxylic acid A solution of 1.02 g (2 mmol) of 7-[3-t-butoxycarbonylamino-1-pyrrolidinyl]-6,8-difluoro-1-(4-fluorophenyl)-1,4-dihydro-4-oxo-3-quinolinecarboxylic acid and 25 ml of trifluoroacetic acid is stirred at room temperature until gas evolution ceases. The solvent is evaporated and the residue treated with 1N sodium hydroxide and diluted with water. The pH is adjusted to 5.5 with 6N hydrochloric acid. The precipitate is filtered washed with water and ether to give the title compound.

We claim:

1. A compound of the formula

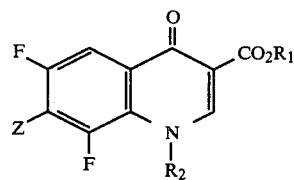

wherein Z is

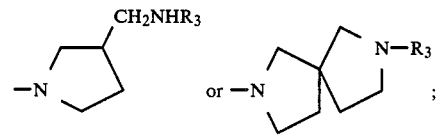

wherein Z is $R_1$ is hydrogen, alkyl having from one to six carbon atoms or a cation; $R_2$ is phenyl or phenyl substituted by halogen, alkyl, alkoxy, hydroxy, amino, monoalkylamino, dialkylamino or trifluoromethyl, 2-, 3-, or 4-pyridine, 2- or 3-thiophene, 2-imidazole, 2-oxazole or 2-thiazole; $R_3$ is hydrogen, alkyl having from one to four carbon atoms or cycloalkyl having three to six carbon atoms; or a pharmaceutically acceptable acid addition or base salt thereof.

2. A compound as claimed in claim 1, wherein $R_1$ is hydrogen or a pharmaceutically acceptable base salt thereof.

3. A compound as claimed in claim 2, wherein Z is

and $R_3$ is hydrogen, methyl, or ethyl.

4. A compound as claimed in claim 3, wherein $R_2$ is p-fluorophenyl, p-aminophenyl, p-monoalkylaminophenyl, p-dialkylaminophenyl, 2-, 3-, or 4-pyridine, or 2-thiazole.

5. A compound as claimed in claim 2, wherein Z is

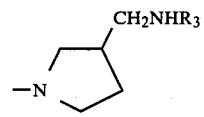

in which $R_3$ is hydrogen, methyl, ethyl, 1- or 2-propyl.

6. A compound as claimed in claim 5, wherein $R_2$ is p-fluorophenyl, p-aminophenyl, p-monoalkylaminophenyl, p-dialkylaminophenyl, 2-, 3-, or 4-pyridine, or 2-thiazole.

7. A compound as claimed in claim 6, and being 7-[3[(ethylamino)methyl]-1-pyrrolidinyl]-6,8-dihydro-4-oxo-1-phenyl-3-quinoline-carboxylic acid.

8. A compound as claimed in claim 6, and being 7-[3-(aminomethyl)-1-pyrrolidinyl]-6,8-difluoro-1,4-dihydro-4-oxo-1-phenyl-3-quinoline-carboxylic acid.

9. A compound as claimed in claim 6, and being 7-[3-[(ethylamino)methyl]-1-pyrrolidinyl]-6,8-difluoro-1-(4-fluorophenyl)-1,4-dihydro-4-oxo-3-quinolinecarboxylic acid.

10. A compound as claimed in claim 6 and being 7-[3-(aminomethyl)-1-pyrrolidinyl]-6,8-difluoro-1-(4-fluorophenyl)-1,4-dihydro-4-oxo-3-quinolinecarboxylic acid.

11. A pharmaceutical composition comprising an antibacterially effective amount of a compound as claimed in claim 1 together with a pharmaceutically acceptable carrier.

12. The method of treating bacterial infections in mammals which comprises administering to said mammal a pharmaceutical composition as claimed in claim 11.